United States Patent [19]

Burd et al.

[11] Patent Number: 4,699,706

[45] Date of Patent: Oct. 13, 1987

[54] METHOD AND APPARATUS FOR EXTRACTION OF SPECIES FROM ELECTROPHORESIS MEDIA

[75] Inventors: Samuel Burd, Oakland; Daniel Y. Chu, San Francisco, both of Calif.

[73] Assignee: Bio-Rad Laboratories, Inc., Richmond, Calif.

[21] Appl. No.: 868,964

[22] Filed: May 30, 1986

[51] Int. Cl.[4] .................... G01N 27/28; B01D 13/00; B01D 35/06

[52] U.S. Cl. ................ 204/301; 204/299 R; 204/182.3; 204/182.8; 204/180.1

[58] Field of Search ............ 204/180.1, 182.3, 299 R, 204/301, 182.8, 182.6, 182.1, 182.7, 415, 416, 417, 418, 419, 420; 210/445, 446, 232, 927

[56] References Cited

U.S. PATENT DOCUMENTS

| | | | |
|---|---|---|---|
| 2,614,976 | 10/1952 | Patnode et al. | 204/418 |
| 3,533,933 | 10/1970 | Strauch | 204/182.8 |
| 3,579,433 | 5/1971 | Dahlgren | 204/299 R |
| 3,773,648 | 11/1973 | Van Welzen et al. | 204/182.8 X |
| 3,980,546 | 9/1976 | Caccavo | 204/182.8 X |
| 4,552,640 | 11/1985 | Kartenbeck | 204/301 |

Primary Examiner—John F. Niebling
Assistant Examiner—John S. Starsiak, Jr.
Attorney, Agent, or Firm—Townsend and Townsend

[57] ABSTRACT

Electrophoretic extraction of molecular species from a separation medium such as a gel segment is achieved by placing the separation medium in a tube closed at one end by a retaining material such as glass frit, and sealing the closed end of the tube against the mouth of a receiving cup which has a semi-permeable membrane (such as a dialysis membrane) for its bottom. The tube with receiving cup attached is inserted in a tube electrophoresis cell such as those commonly used in analytical laboratories. As current passes through the tube, the molecular species migrates from the separation medium to pass through the retaining frit and collect on the membrane for subsequent recovery.

7 Claims, 4 Drawing Figures

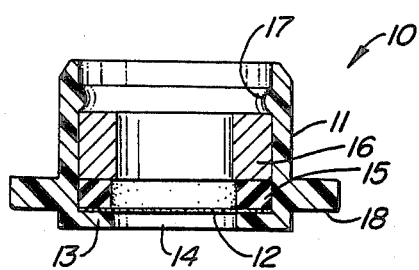
FIG._1.
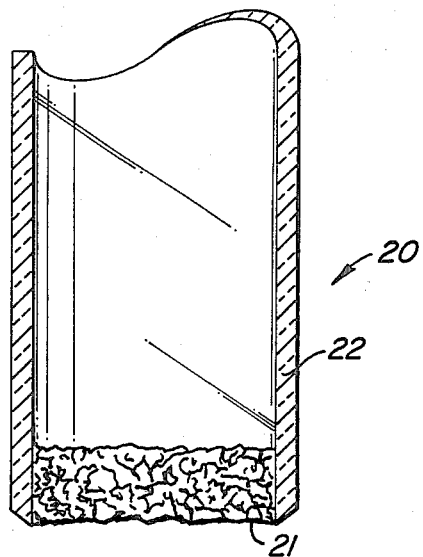
FIG._2.
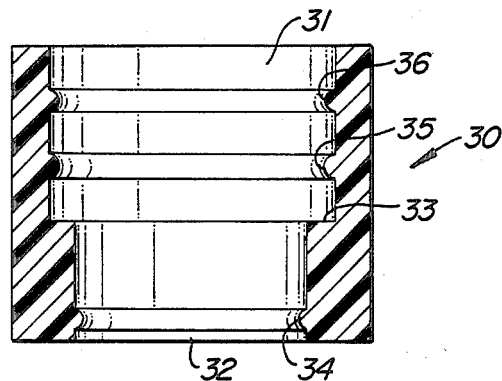
FIG._3.

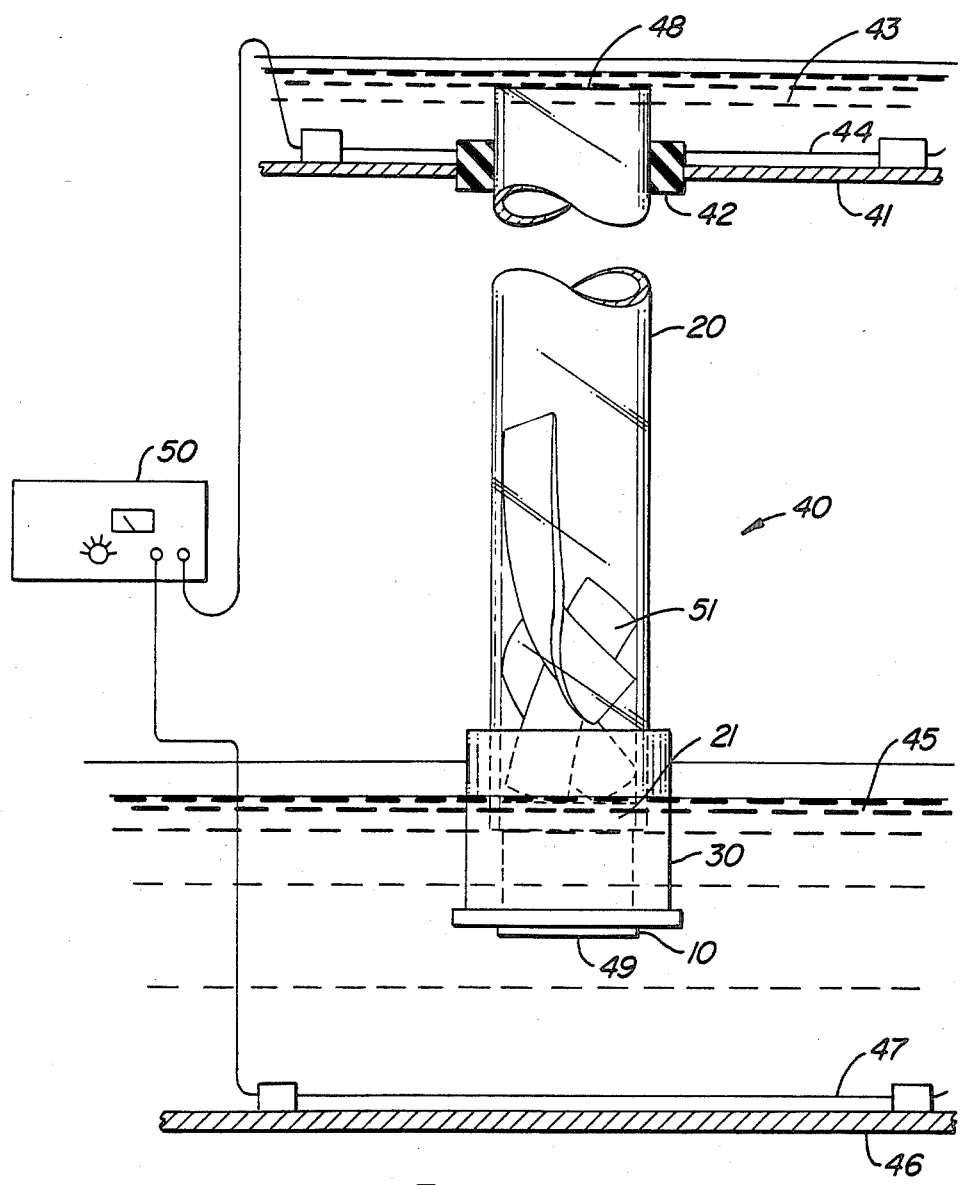
FIG._4.

METHOD AND APPARATUS FOR EXTRACTION OF SPECIES FROM ELECTROPHORESIS MEDIA

BACKGROUND OF THE INVENTION

This invention relates to electrophoretic extractions, and particularly to the extraction and concentration of substances from support media following separations in the media.

Many separation processes, including chromatographic processes, density-gradient centrifugation processes, and various types of electrophoresis, occur in solid or semi-solid separation media such as gels. Once the components of a sample mixture have been separated into discrete regions (bands or zones) in the separation medium, it is frequently desirable to isolate the species individually for either preparative or analytical purposes. This is done by cutting the separation medium into slices or segments, each containing one species. The slice or segment is then placed in an electrophoresis chamber, where the species is caused to migrate out of the support medium to be concentrated in a receiving vessel from which it can be readily removed.

SUMMARY OF THE INVENTION

The present invention resides in a novel device for electrophoretic extraction, which can be inserted into typical laboratory cells designed for tube electrophoresis, and used by running the cell itself. The device has the further advantage of simple and inexpensive yet leak-proof construction and quick assembly.

In one aspect, the invention resides in a receiving cup which incorporates a membrane impermeable to the species to be collected in a manner in which the membrane can be readily inserted and removed. In another aspect, the invention resides in an assembly comprising the receiving cup, a tube closed at one end with a material which permits passage of the species to be collected but not the support medium, and a sleeve which receives both the receiving cup and tube, sealing around each to permit migration of the species through the closed end of the tube into the receiving cup. Finally, the invention resides in a method of using such a tube and receiving cup in a tube electrophoresis cell.

BRIEF DESCRIPTION OF THE DRAWINGS

FIG. 1 is a sectional view, side elevation, of an illustrative example of a receiving cup in accordance with the present invention.

FIG. 2 is a sectional view, side elevation, of an illustrative example of a tube element in accordance with the present invention.

FIG. 3 is a sectional view, side elevation, of an illustrative example of a connecting sleeve designed to join the receiving cup and tube elements of FIGS. 1 and 2, respectively, in fluid-tight manner.

FIG. 4 shows the elements of FIGS. 1, 2 and 3 combined for use and installed in a cell designed for tube electrophoresis, the cell shown in sectional view.

DETAILED DESCRIPTION OF THE INVENTION AND PREFERRED EMBODIMENTS

The receiving cup of the present invention is an open-top vessel whose bottom is closed off by a membrane which permits the passage of water and electric current and yet is impermeable to the species sought to be collected. An illustrative construction is shown in FIG. 1. Here, the receiving cup 10 is comprised of a sleeve 11 which forms the side walls of the cup, and a membrane 12 forming the cup bottom. The membrane material is not critical, and can be any of a wide variety of materials. Particularly useful membranes are dialysis membrane disks. Spectrapor dialysis tubing material, Spectrum Medical Industries, Los Angeles, Calif. has been used effectively.

The membrane 12 rests on an internal shoulder 13 on the inner wall of the sleeve 11. The shoulder is transverse to the sleeve axis and extends the full circumference of the sleeve. The membrane 12 when resting on the shoulder spans the entire opening 14 at the lower end of the sleeve.

The membrane is held in place by a gasket 15 and a retaining ring 16, both of which are held in place by a protrusion 17 on the inner wall of the sleeve. The protrusion in this embodiment is a rib, transverse to the axis of the sleeve and extending around the full circumference. The gasket 15 is of resilient material such as, for example, silicone rubber, and is sized to fit snugly inside the sleeve 11, and preferably to rest fully on the shoulder 13. The retaining ring 16 is of substantially nondeformable material such as, for example, polyethylene. The rib 17 is positioned to create a tight fit when membrane, gasket and retaining ring are all inserted, and to compress the three together, deforming the gasket 15 sufficiently to seal the membrane 12 between it and the shoulder 13. Fluid passage will then occur only through the membrane 12 in the axial direction of the sleeve 11.

In the embodiment shown, the receiving cup further contains an external flange 18 near the membrane end. This flange is to facilitate positioning of the receiving cup in the full assembly and connecting it with the other features of the apparatus, as shown in the other Figures and described below.

Turning to FIG. 2, a tube 20 is shown. The tube is sized to accommodate the pieces of support medium which contains the species to be extracted and collected. The support medium is generally comprised of gel slices, and the species are typically proteins or nucleic acids which have been electrophoretically isolated from mixtures. The tube 20 is further sized to replace electrophoresis tubes in a common laboratory tube electrophoresis cell. Differences between this tube and the tubes normally used in the cell are that this tube is used without being filled with separation medium (such as gel), and is closed at the bottom end with a material 21 which supports the gel slices, or whatever support medium the species to be collected is present in, and retains them while the species migrates out under the influence of an electric current. A glass frit is particularly useful as the enclosing material 21. The tube wall 22 may be any fluid-impermeable material, preferably transparent, and most preferably glass.

FIG. 3 illustrates a sleeve 30 which joins the receiving cup 10 to the tube 20, sealing the two together for use in the electrophoresis cell. The sleeve is open at both top and bottom, the top opening 31 sized to receive the tube and the bottom opening 32 sized to receive the open end of the receiving cup 10. In the embodiments shown, the tube and receiving cup are of different outer diameters, with a corresponding difference in the diameters of the top and bottom openings 31, 32 of the connecting sleeve 30. An internal shoulder 33 along the inner wall of the connecting sleeve receives the end face of whichever of the tube and receiving cup has the larger diameter. In the embodiments shown, the tube has the larger diameter. The shoulder 33 thus guides the insertion of both parts by limiting the depth of insertion of the tube 20 and hence the receiving cup 10 once the tube 20 has been inserted.

Seals around the peripheries of both the tube and the receiving cup are achieved by sealing ribs 34, 35, 36 in the internal wall of the connecting sleeve. At least one such rib encircles each of the tube and receiving cup. In the preferred embodiment shown, two ribs encircle the tube. All three ribs function both to secure the parts together and to create a fluid-tight seal, permitting fluid passage only in the axial direction through the tube and receiving cup.

The connecting sleeve 30 is preferably of a resilient material such as, for example, silicone rubber.

The components shown in FIGS. 1, 2 and 3 are combined in an assembly 40 in FIG. 4, which shows the assembly installed in a cell designed for tube electrophoresis. The assembly occupies the position normally occupied by a gel-filled tube. Thus, the tube 20 of the assembly is suspended from a plate 41 with a gasket ring seal 42, the plate 41 forming the floor of a portion of the cell holding the upper buffer solution 43. An electrode 44 is immersed in the upper buffer solution 43. The vessel containing the upper buffer solution is typically mounted on a rack which is placed inside a tank containing the lower buffer solution 45. In Figure 4, only the floor 46 of the tank is shown. An electrode 47 is secured to the floor 46 of the tank to be immersed in the lower buffer solution 45.

When the assembly 40 consisting of the tube 20, receiving cup 10 and connecting sleeve 30 are properly mounted, the upper open end 48 of the tube is immersed in the upper buffer solution 43 and the lower end 49 of the receiving cup is immersed in the lower buffer solution 45. Upper buffer solution also fills the tube 20 and receiving cup 10. Electric current from a power supply 50 passes between the electrodes 44, 47, causing electrophoretic migration of molecular species from the support medium 51 (shown here as electrophoresis gel slices) past the frit 21 downward into the receiving cup 10 to collect at the dialysis membrane forming the bottom of the cup. When extraction is complete, the assembly 40 is removed from the cell, and the cup 10 is withdrawn from the connecting sleeve 30. The cup will contain a small amount of buffer solution containing the species in concentrated form. This may be removed in any conventional manner, preferably by pipette.

The foregoing description is offered primarily for purposes of illustration. It will be readily apparent to those skilled in the art that variations and modifications of the structures and methods described herein may be made without departing from the spirit and scope of the invention, as defined by the claims.

What is claimed is:

1. A receiving cup for collecting species electrophoretically extracted from a support medium, said receiving cup comprising:
    a sleeve containing a transverse internal shoulder extending the full circumference thereof;
    a membrane impermeable to said species, sized to rest on said shoulder;
    a gasket of resilient material sized to fit snugly inside said sleeve and to rest on said shoulder above said membrane;
    a ring of substantially nondeformable material sized to fit snugly and completely within said sleeve and to rest on said gasket; and
    a protrusion on the interior wall of said sleeve of sufficient size to retain said ring, said protrusion positioned to compress said ring, said gasket and said membrane together between itself and said shoulder.

2. A receiving cup in accordance with claim 1 in which said protrusion is a transverse rib extending the full circumference of said sleeve.

3. Apparatus for separating species from a support medium during electrophoretic migration of said species, said apparatus comprising:
    a tube closed at one end with a first material permeable to said species and impermeable to said support medium;
    a vessel open at the top and closed at the bottom with a second material permeable to water and impermeable to said species;
    a sleeve having first and second open ends sized to receive respectively said closed end of said tube and said top of said vessel;
    a first rib on the interior wall of said sleeve to engage the exterior of said tube; and
    a second rib on the interior wall of said sleeve to engage the exterior of the side wall of said vessel.

4. Apparatus for separating species from a support medium during electrophoretic migration of said species, said apparatus comprising:
    a tube closed at one end with a first material permeable to said species and impermeable to said support medium;
    a vessel open at the top and closed at the bottom with a second material permeable to water and impermeable to said species; and
    a sleeve having first and second open ends sized to receive respectively said closed end of said tube and said top of said vessel, and an internal shoulder to abut the inserted end of one of said tube and said vessel.

5. Apparatus for separating species from a support medium during electrophoretic migration of said species, said apparatus comprising:
    a tube closed at one end with a first material permeable to said species and impermeable to said support medium;
    a vessel open at the top and closed at the bottom with a second material permeable to water and impermeable to said species, said tube and said vessel being of different outer diameters; and
    a sleeve having first and second open ends sized to receive respectively said closed end of said tube and said top of said vessel, and an internal shoulder to abut the inserted end of the larger diameter one of said tube and said vessel.

6. Apparatus for separating species from a support medium during electrophoretic migration of said species, said apparatus comprising:
    a tube closed at one end with a first material permeable to said species and impermeable to said support medium;
    a vessel open at the top and closed at the bottom with a second material permeable to water and impermeable to said species;
    a sleeve having first and second open ends sized to receive respectively said closed end of said tube and said top of said vessel; and a flange extending laterally from the bottom of said vessel into said sleeve.

7. Apparatus for separating species from a support medium during electrophoretic migration of said species, said apparatus comprising:
 (a) a tube closed at one end with a first material permeable to said species and impermeable to said support medium;
 (b) a receiving cup comprising:
  (i) a first sleeve containing a transverse internal shoulder extending the full circumference thereof;
  (ii) a membrane impermeable to said species, sized to rest on said shoulder;
  (iii) a gasket of resilient material sized to fit snugly inside said sleeve and to rest on said shoulder above said membrane;
  (iv) a ring of substantially nondeformable material sized to fit snugly within said sleeve and to rest on said gasket; and
  (v) a protrusion on the interior wall of said sleeve of sufficient size to retain said ring, said protrusion positioned to compress said ring, said gasket and said membrane together between itself and said shoulder; and
 (c) a second sleeve having first and second open ends sized respectively to receive said closed end of said tube and said first sleeve.

* * * * *